(12) United States Patent
Pianca et al.

(10) Patent No.: US 8,249,721 B2
(45) Date of Patent: Aug. 21, 2012

(54) METHOD FOR FABRICATING A NEUROSTIMULATION LEAD CONTACT ARRAY

(75) Inventors: Anne Margaret Pianca, Santa Monica, CA (US); Ariadne Genevieve Smith, Ashland, OR (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 229 days.

(21) Appl. No.: 12/501,979

(22) Filed: Jul. 13, 2009

(65) Prior Publication Data

US 2011/0005829 A1    Jan. 13, 2011

(51) Int. Cl.
*A61N 1/05* (2006.01)

(52) U.S. Cl. .......................... 607/116; 607/45

(58) Field of Classification Search .............. 607/45, 607/116, 117; 600/372–374, 377, 378
See application file for complete search history.

(56) References Cited

U.S. PATENT DOCUMENTS

| | | | |
|---|---|---|---|
| 5,374,285 A | 12/1994 | Vaiani et al. | |
| 5,855,552 A * | 1/1999 | Houser et al. | 600/374 |
| 5,869,804 A | 2/1999 | Mueller et al. | |
| 5,991,650 A | 11/1999 | Swanson et al. | |
| 6,185,463 B1 * | 2/2001 | Baudino | 607/119 |
| 6,210,339 B1 | 4/2001 | Kiepen et al. | |
| 6,366,820 B1 | 4/2002 | Doan et al. | |
| 6,440,488 B2 | 8/2002 | Griffin, III et al. | |
| 6,471,699 B1 * | 10/2002 | Fleischman et al. | 600/374 |
| 6,505,401 B1 | 1/2003 | Doan | |
| 6,757,970 B1 * | 7/2004 | Kuzma et al. | 29/847 |
| 6,952,616 B2 | 10/2005 | Wessman et al. | |
| 7,039,470 B1 | 5/2006 | Wessman | |
| 7,047,081 B2 | 5/2006 | Kuzma | |
| 7,047,627 B2 | 5/2006 | Black et al. | |
| 7,239,922 B1 * | 7/2007 | Boogaard et al. | 607/116 |
| 2005/0113899 A1 | 5/2005 | Cross | |

* cited by examiner

*Primary Examiner* — Carl H Layno
*Assistant Examiner* — Eugene Wu
(74) *Attorney, Agent, or Firm* — Frommer Lawrence & Haug LLP; Bruce E. Black

(57) ABSTRACT

A lead includes a lead body defining a lumen extending through the lead body; a conductor disposed in the lumen; a slit extending from an exterior of the lead body through at least a portion of the lead body to the lumen; and a contact strip. A portion of the contact strip is optionally disposed in the slit and is in contact with a portion of the conductor. A second portion of the contact strip is optionally wrapped around the lead body. A method of making a lead includes disposing one or more conductors in a lumen of a lead body; forming a slit from an exterior of the lead body to the lumen to access a portion of at least one conductor disposed in the lumen; coupling a flat contact strip to the portion of the conductor, and wrapping the contact strip around the lead body.

15 Claims, 7 Drawing Sheets

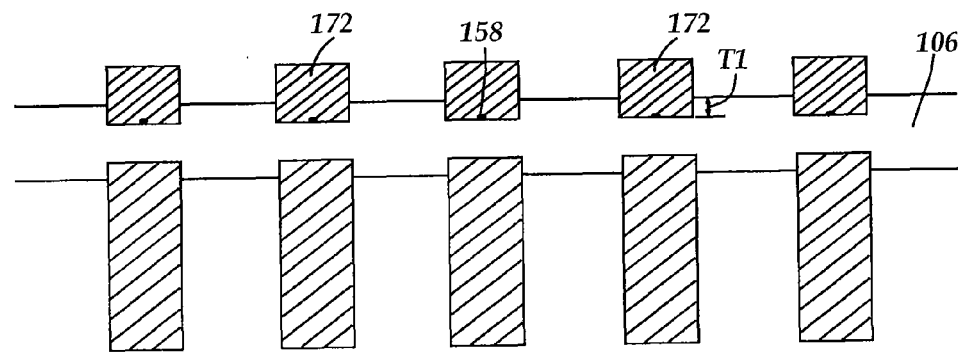
Fig. 4
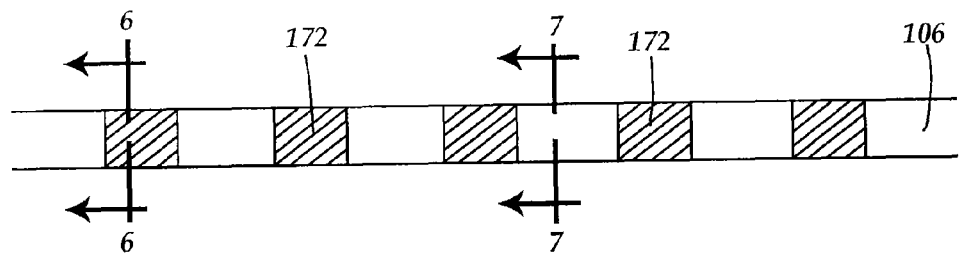
Fig. 5
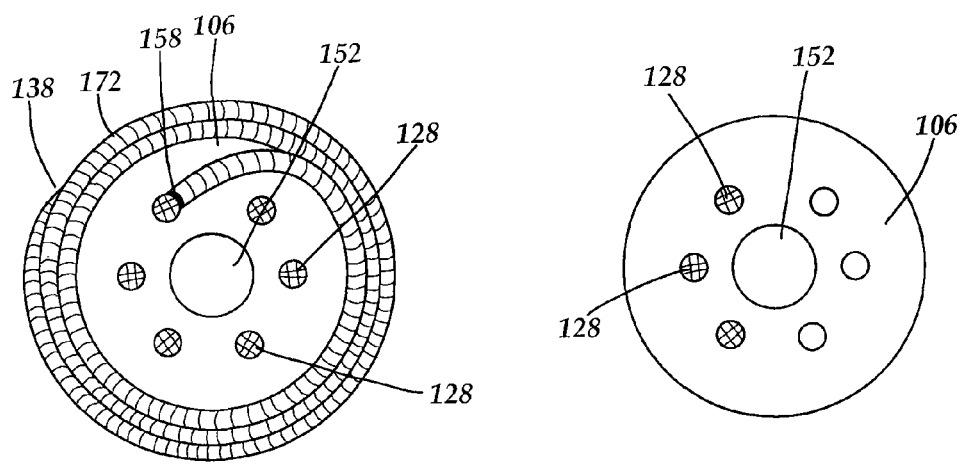
Fig. 6
Fig. 7

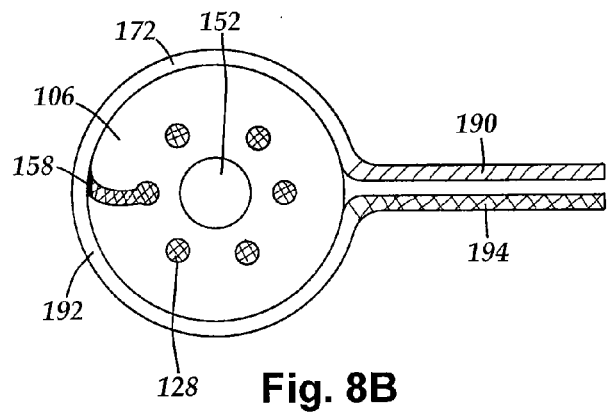
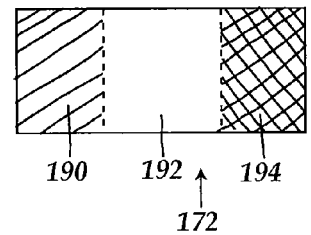
Fig. 8B  Fig. 8A
Fig. 9
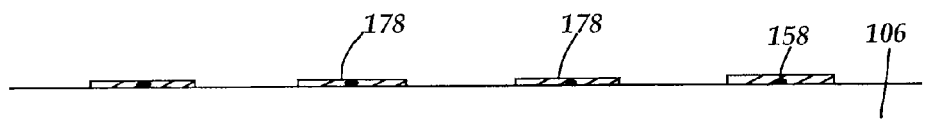
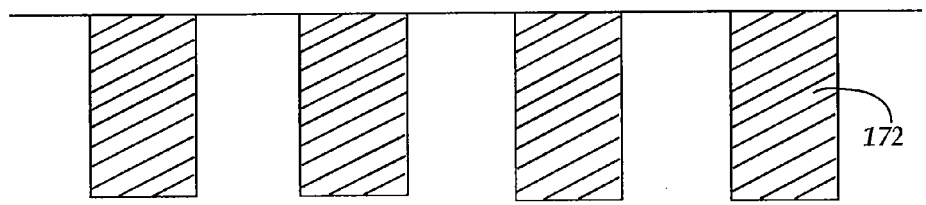
Fig. 10
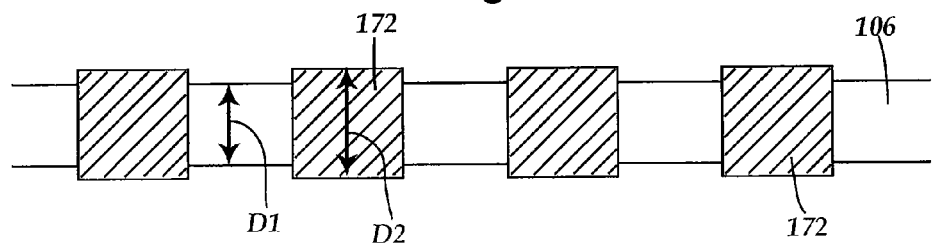
Fig. 11
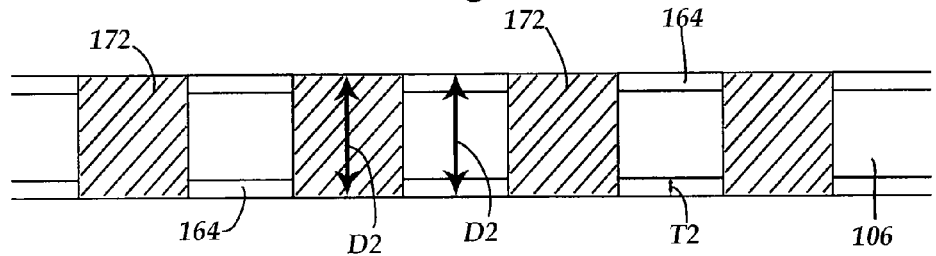

METHOD FOR FABRICATING A NEUROSTIMULATION LEAD CONTACT ARRAY

FIELD

The present invention is directed to the area of implantable electrical stimulation systems and methods of making and using the systems. The present invention is also directed to implantable electrical stimulation leads having contact strips that are wrapped around the lead body, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead includes a lead body defining a first lumen extending through the lead body; a first conductor disposed in the first lumen; a first slit extending from an exterior of the lead body through at least a portion of the lead body to the first lumen; and a first contact strip. In some embodiments, a first portion of the first contact strip is disposed in the first slit and is in contact with a portion of the first conductor and a second portion of the first contact strip is wrapped around the lead body.

In one embodiment, a method of making a lead includes disposing one or more conductors in a first lumen of a lead body; forming a first slit from an exterior of the lead body to the first lumen to access a portion of at least one of the one or more conductors disposed in the first lumen; coupling a first contact strip to the portion of at least one of the one or more conductors; and wrapping the first contact strip around the lead body. In some embodiments, the first contact strip is flat.

In another embodiment, a method of making a lead includes forming a slit in a lead body, wherein the lead body defines at least one lumen extending along the length of the lead body, wherein a plurality of conductor are disposed in the at least one lumen, and wherein the slit extends from an exterior of the lead body to a one of the at least one lumen. In some embodiments, the method further includes inserting a portion of a contact strip into the slit; contacting the portion of the contact strip with at least one of the plurality of conductors; and wrapping the contact strip around the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4 is a schematic perspective view of one embodiment of an end portion of a lead body coupled to contact strips, according to the invention;

FIG. 5 is a schematic perspective view of one embodiment, of an end portion of a lead, according to the invention;

FIG. 6 is a cross-sectional view of the end portion of the lead of FIG. 5 at line 6-6;

FIG. 7 is a cross-sectional view of the end portion of the lead of FIG. 5 at line 7-7;

FIG. 8A is a schematic perspective view of one embodiment of a contact strip, according to the invention;

FIG. 8B is a cross-sectional view of one embodiment of an end portion of a lead body with a contact strip wrapped around the lead body, according to the invention;

FIG. 9 is a schematic perspective view of one embodiment of an end portion of a lead body coupled to contact strips, according to the invention;

FIG. 10 is a schematic perspective view of one embodiment of an end portion of a lead, according to the invention;

FIG. 11 is a schematic perspective view of one embodiment of an end portion of a lead, according to the invention;

DETAILED DESCRIPTION

The present invention is directed to the area of implantable electrical stimulation systems and methods of making and using the systems. The present invention is also directed to implantable electrical stimulation leads having contact strips that are wrapped around the lead body, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
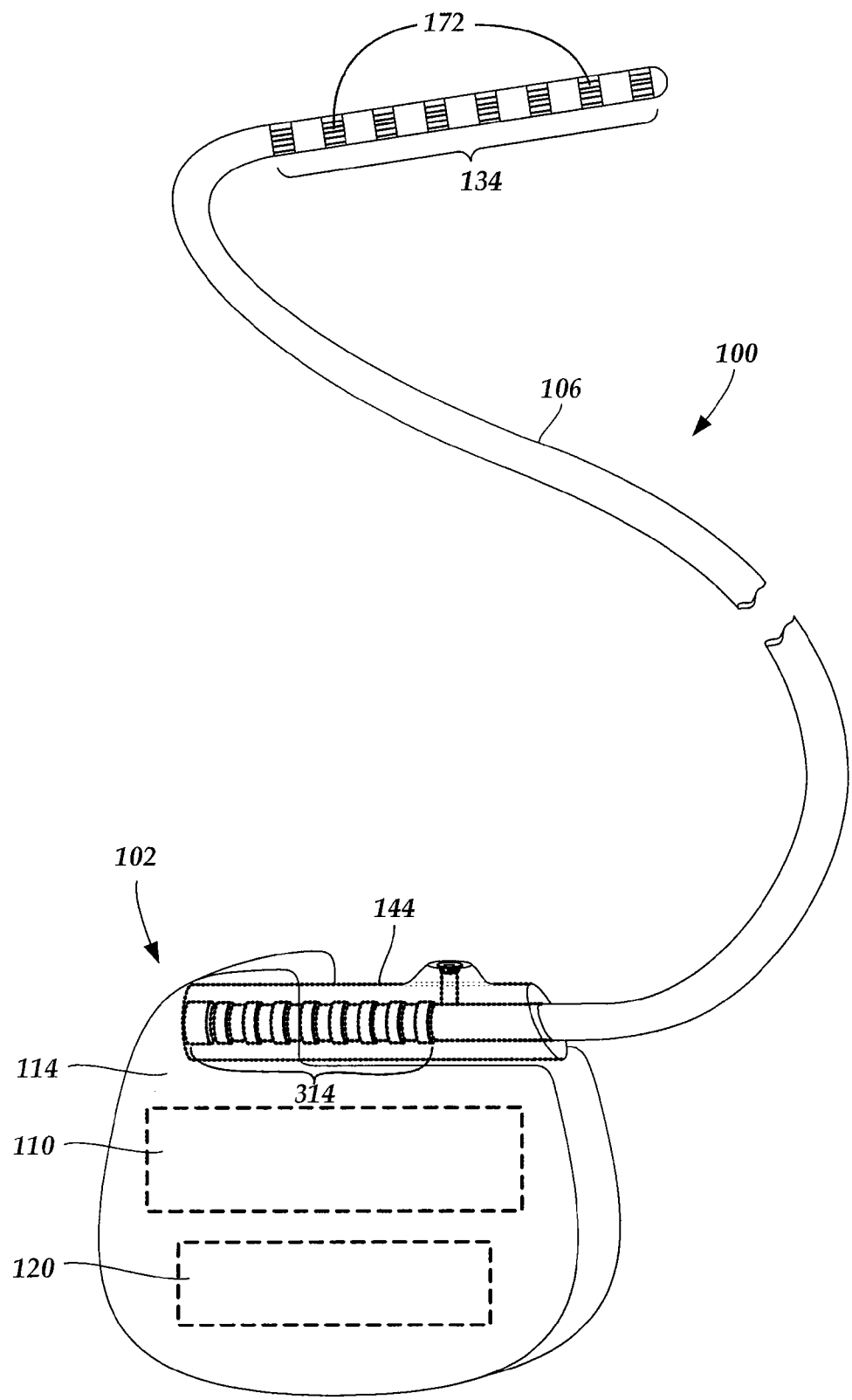
FIG. 1 is a schematic perspective view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead body 106 coupled to the control module 102. Each lead body 106 typically includes an array of electrodes 134. The control module 102 typically includes an electronic subassembly 110 and an optional power source 120 disposed in a sealed housing 114. The control module 102 typically includes a connector 144 (FIGS. 1 and 2; see also 322 and 350 of FIG. 3) into which the proximal end of the one or more lead bodies 106 can be plugged to make an electrical connection via conductive contacts on the control module 102 and terminals (e.g., 310 in FIG. 2 and 336 in FIG. 3) on each of the one or more lead bodies 106. In at least some embodiments, a lead body 106 is isodiametric along a longitudinal length of the lead body 106. In addition, one or more lead extensions 324 (see FIG. 3) can be disposed between the one or more lead bodies 106 and the control module 102 to extend the distance between the one or more lead bodies 106 and the control module 102 of the embodiment shown in FIG. 1.

The electrical stimulation system or one or more components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be one, two, three, four, five, six, seven, eight, nine, ten, eleven, twelve, thirteen, fourteen, fifteen, sixteen, or more electrodes 134. As will be recognized, other numbers of electrodes 134 may also be used.

The electrodes of one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), extruding, casting, and the like. The non-conductive material typically extends from the distal end of the one or more lead bodies 106 to the proximal end of each of the one or more lead bodies 106.

Terminals (e.g., 310 in FIG. 2 and 336 in FIG. 3) are typically disposed at the proximal end of the one or more lead bodies 106 of the electrical stimulation system 100 for connection to corresponding conductive contacts (e.g., 314 in FIGS. 1 and 2; 340 in FIG. 3) in connectors (e.g., 144 in FIGS. 1 and 2; 322 and 350 in FIG. 3) disposed on, for example, the control module 102 (or to conductive contacts on a lead extension, an operating room cable, or an adaptor). Conductors 128 (see, e.g., FIGS. 6, 7, 8B and 12-14) extend from the terminals (e.g., 310 in FIG. 2 and 336 in FIG. 3) to the electrodes 134. Typically, one or more electrodes 134 are electrically coupled to a terminal (e.g., 310 in FIG. 2 and 336 in FIG. 3). In at least some embodiments, each terminal (e.g., 310 in FIG. 2 and 336 of FIG. 3) is only connected to one electrode 134.

The conductors 128 may be embedded in the non-conductive material of the lead body 106 (see, e.g., FIGS. 6, 7, and 8B) or can be disposed in one or more lumens 152 (see, e.g., FIGS. 12-14) extending along the length of the lead body 106. As described above, the electrodes 134 are electrically coupled to the terminals (e.g., 310, 336) via one or more conductors 128. In at least some embodiments, the number of conductors 128 is equal to the number of electrodes 134. In other embodiments, two or more electrodes 134 may be coupled to one of the conductors 128. The conductors may be formed from any conductive, bio-compatible material such as, for example, metals, alloys, and the like, as well as combinations thereof.

There may be one or more lumens 152 that open at, or near, the proximal end of the lead body 106, for example, for inserting a stylet rod to facilitate placement of the lead body 106 within a body of a patient. Additionally, there may also be one or more lumens 152 that open at, or near, the distal end of the lead body 106, for example, for infusion of drugs or medication into the site of implantation of the one or more lead bodies 106. In at least one embodiment, the one or more lumens 152 may be flushed continually, or on a regular basis, with saline, epidural fluid, or the like. In at least some embodiments, the one or more lumens 152 can be permanently or removably sealable at the distal end.

Figure 2:
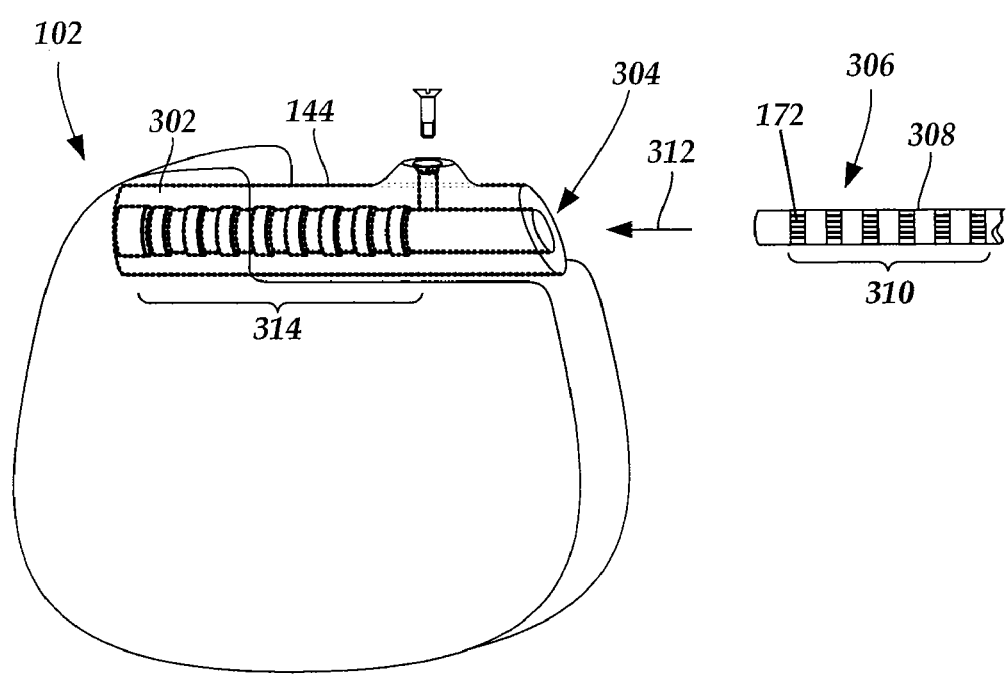
FIG. 2 is a schematic perspective view of one embodiment of a proximal portion of a lead and a control module of an electrical stimulation system, according to the invention.

In at least some embodiments, leads are coupled to connectors disposed on control modules. In FIG. 2, a proximal portion 306 of a lead 308 is shown configured and arranged for insertion into the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3:
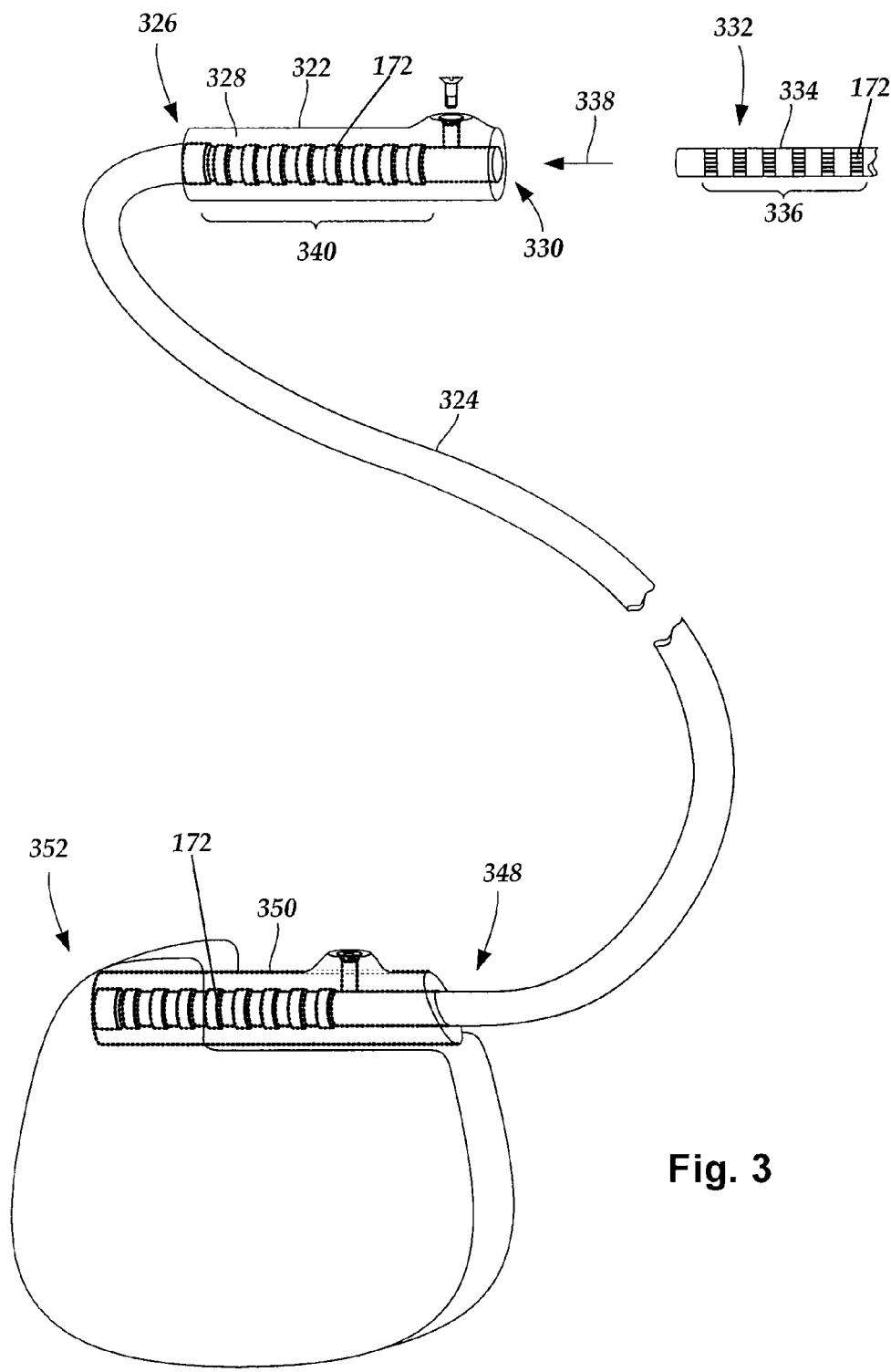
FIG. 3 is a schematic perspective view of one embodiment of a proximal portion of a lead, a lead extension and a control module of an electrical stimulation system, according to the invention.

In FIG. 3, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductors 128 (see, e.g., FIGS. 6, 7, 8B and 12-14) that electrically couple the conductive contacts 340 to a proximal end 348 of the lead extension 324 that is opposite to the distal end 326. In at least some embodiments, the conductors 128 disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3 the proximal end 348 of the lead extension 324 is inserted into a connector 350 disposed in a control module 352.

Returning to FIG. 1, one or more contact strips 172 are wrapped around the lead body 106. The contact strips 172 wrapped around the lead body 106 are electrically coupled to at least one conductor 128 (see e.g., FIGS. 12-14). In some embodiments, more than one contact strip 172 can be coupled to one conductor 128. In some embodiments, more than one conductor 128 can be coupled to one contact strip 172.

In some embodiments, the contact strips 172 wrapped around the lead body 106 and coupled to at least one conductor 128 are electrodes 134 disposed on a distal end of the lead body 106 (see FIG. 1). In other embodiments, the contact strips 172 wrapped around the lead body 106 and coupled to at least one conductor 128 are terminals (e.g., 310, 336) disposed on a proximal end of a lead body 106 or a lead extension 324 (see, e.g., FIGS. 2 and 3). As will be recognized, a lead body 106 can include one or more contact strips 172 that are electrodes 134 as well as one or more contact strips 172 that are terminals (e.g., 310, 336).

The contact strips 172 can be formed from any conductive, bio-compatible material such as, for example, metals, alloys, conductive polymers, conductive carbon, and the like, as well as combinations thereof. There can be any number of contact strips 172 including one, two, three, four, five, six, seven, eight, nine, ten, eleven, twelve, thirteen, fourteen, fifteen, sixteen or more contact strips 172. As will be recognized, if the contact strips 172 form electrodes 134, the number of contact strips 172 can be equal to the number of electrodes 134. If the contact strips 172 form terminals (e.g., 310, 336), the number of contact strips 172 can be equal to the number of terminals (e.g., 310, 336). Likewise, if the contact strips 172 form electrodes 134 as well as terminals (e.g., 310, 336), the number of contact strips 172 can be equal to the number of electrodes 134 and terminals (e.g., 310, 336).

In some embodiments, a method of making a lead comprises disposing one or more conductors 128 in at least one lumen 152 of a lead body 106. In some embodiments, there is an individual lumen 152 for each conductor 128 as illustrated schematically in, for example, FIGS. 12-14. In other embodiments, two or more conductors 128 may extend through one lumen 152. As described above, at least one conductor 128 may optionally be embedded in the non-conductive material of the lead body 106 as illustrated schematically in FIGS. 6, 7 and 8B.

Turning to FIG. 4, in some embodiments, a method of making a lead comprises removing a portion of the lead body 106. As illustrated schematically in FIG. 4, a portion of the lead body 106 can optionally be removed at one or more locations where one or more contact strips 172 will be coupled to conductors 128. A portion of the lead body 106 can be removed by any process known to those of skill in the art such as, for example, ablation, etching, and the like. Removing a portion of the lead body 106 can optionally reduce the diameter of the lead body 106 at particular locations as illustrated schematically in FIG. 4. In some embodiments, the thickness T1 of the portion of the lead body 106 that is removed is such that the lead will be isodiametric after one or more contact strips 172 are wrapped around the lead body 106 as illustrated schematically in FIGS. 4 and 5. In some embodiments, a portion of the lead body 106 is removed such that a portion of a conductor 128 disposed in a lumen 152 of the lead body 106 or embedded in the material of the lead body 106 is exposed. In some embodiments, the location of the portions of the lead body 106 that are removed are staggered such that a different conductor 128 is exposed at each location where a portion of the lead body 106 is removed.

Figure 12:
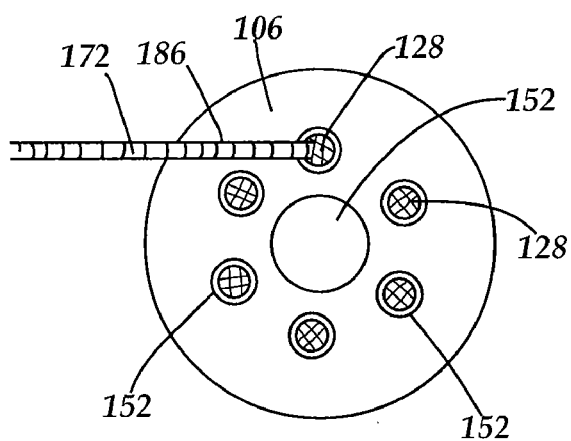
FIG. 12 is a cross-sectional view of one embodiment of an end portion of a lead body with a portion of a contact strip disposed in a slit in the lead body, according to the invention.
Figure 13:
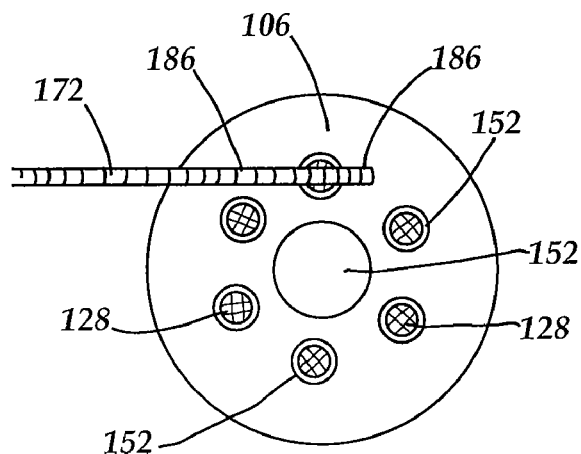
FIG. 13 is a cross-sectional view of one embodiment of an end portion of a lead body with a portion of a contact strip disposed in a slit in the lead body, according to the invention.
Figure 14:
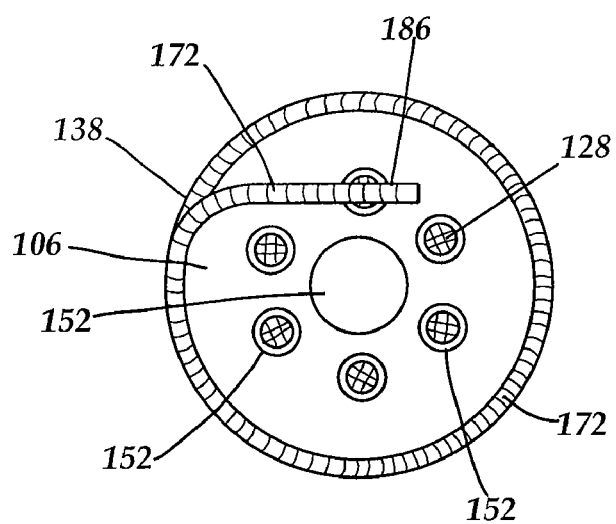
FIG. 14 is a cross-sectional view of one embodiment of an end portion of a lead body with a first portion of a contact strip disposed in a slit in the lead body and a second portion of a contact strip wrapped around the lead body, according to the invention.

In some embodiments, a method of making a lead comprises forming at least one slit 186 in the lead body 106 (see, e.g., FIGS. 12-14). In some embodiments, a slit 186 is formed from an exterior of the lead body 106 to at least one lumen 152 of the lead body 106. The slit 186 in the lead body 106 can be formed by any process known to those of skill in the art such as, for example, laser ablation, etching, mechanically piercing or cutting the lead body 106, or the like. At least a portion of one or more conductors 128 disposed in a lumen 152 or embedded in the non-conductive material of the lead body 106 is accessible through the slit 186 formed in the lead body 106.

In some embodiments, a method of making a lead comprises coupling at least a portion of at least one contact strip 172 to a portion of at least one conductor 128 that is disposed in a lumen 152 or embedded in a non-conductive material of the lead body 106. The conductor 128 is optionally accessible through a slit 186 in the lead body 106. Alternatively or additionally, the conductor 128 may be accessible when a portion of the lead body 106 is removed. In some embodiments, the slit 186 extends from an exterior of the lead body 106 to at least one conductor 128 disposed in the lead body 106. For example, the slit 186 may optionally extend from an exterior of the lead body 106 to a conductor 128 disposed in a lumen 152. The slit 186 may optionally extend from an exterior of the lead body 106, through at least a portion of the lead body 106, and through at least one lumen 152 into a second portion of the lead body 106. In some embodiments, two or more slits 186 are formed in the lead body 106. The two or more slits 186 can optionally be formed such that the same conductor or two or more different conductors 128 can be accessed. For example, the location of two or more slits 186 can optionally be staggered around the circumference of the lead body 106 to expose a different conductor 128 with each slit 186. At least one slit 186 can optionally be formed at a proximal end of the lead body 106, at a distal end of the lead body 106, or at both the proximal end and the distal end of the lead body 106.

The contact strip 172 can be coupled to at least a portion of the conductor 128 by any process known to those of skill in the art such as, for example, welding (e.g., resistance welding, laser welding), crimping, contact with a pad, contact between the conductor 128 and the contact strip 172, or the like. In some embodiments, at least a portion of the conductor 128 can be disposed through the slit 186 in the lead body 106 and coupled to the contact strip 172 as illustrated schematically in FIG. 8B.

In other embodiments, at least a portion of the contact strip 172 is inserted into the slit 186 in the lead body 106 and is coupled to the conductor 128 as illustrated schematically in FIGS. 12-14. For example, at least a portion of the contact strip 172 can optionally be inserted into the slit 186 and into at least one lumen 152, where the portion of the contact strip 172 is coupled to the conductor 128 as illustrated schematically in FIGS. 12-14. At least a portion of two or more contact strips 172 can optionally be inserted into a slit 186 or into two or more different slits 186.

In still other embodiments, a conductive material is disposed in the slit 186 to electrically couple the conductor 128 disposed in the lumen 152 to the contact strip 172 disposed on an exterior surface of the lead body 106.

The contact strip 172 can be coupled to a conductor 128 at any location on the contact strip 172. For example, the contact strip 172 can optionally be coupled to a conductor 128 at a center portion 192 of the contact strip 172 as illustrated schematically in FIG. 8B, at an end portion (190, 194; see FIG. 8A) of the contact strip 172 as illustrated schematically in FIG. 4, or at an end 178 of the contact strip 172 as illustrated schematically in FIG. 9. In FIGS. 4, 8B and 9, the contact strips 172 are coupled to conductors 128 at contact interface 158.

In some embodiments, the contact strips 172 are flat. That is, in some embodiments, the contact strips 172 are not curved prior to wrapping the contact strips 172 around the lead body 106. In one embodiment, flat contact strips 172 coupled to conductors 128 of a lead body 106 are illustrated schematically in FIG. 4. In another embodiment, flat contact strips 172 coupled to conductors 128 of a lead body 106 are illustrated schematically in FIG. 9.

A contact strip 172 can have a shape in the form of a square, triangle, rectangle, parallelogram, ellipse, circle or any other regular or irregular shape. In some embodiments, at least one contact strip 172 has a shape in the form of a rectangle as illustrated schematically in FIGS. 4 and 9. In some embodiments, all of the contact strips 172 have a shape in the form of a rectangle. The contact strips 172 wrapped around a lead body 106 can optionally have the same or different shapes.

In some embodiments, a method of making a lead comprises wrapping at least one contact strip 172 around a lead body 106. In some embodiments, two or more contact strips 172 are wrapped around the lead body 106. In one embodiment, a lead body 106 with a plurality of contact strips 172 wrapped around the lead body 106 is illustrated schematically in FIG. 5. In another embodiment, a lead body 106 with a plurality of contact strips 172 wrapped around the lead body 106 is illustrated schematically in FIG. 10.

The two or more contact strips 172 can optionally be wrapped around the lead body 106 one at a time or simultaneously. Wrapping two or more contact strips 172 around a lead body 106 simultaneously to form electrodes 134, terminals (e.g., 310, 336), or both electrodes 134 and terminals (e.g., 310, 336) advantageously allows leads to be made more quickly and in a less labor-intensive manner.

In some embodiments, the contact strip 172 can be wrapped around the lead body 106 two or more times to form two or more layers of the contact strip 172 around the lead body as illustrated schematically in FIG. 6. A contact strip 172 can optionally be wrapped around a lead body 106 such that there is one layer of the contact strip 172 around the lead body 106 as illustrated schematically in FIGS. 8B and 14.

In one embodiment, a contact strip 172 is illustrated schematically in FIG. 8A. The contact strip 172 illustrated in FIG. 8A includes a first end portion 190, a second end portion 194 and a center portion 192. The contact strip 172 illustrated schematically in FIG. 8A is shown wrapped around a lead body 106 in FIG. 8B such that the center portion 192 forms a single layer around the lead body 106. The first end portion 190 and the second end portion 194, which are not wrapped around the lead body, may optionally be removed. A portion of a contact strip 172, such as a portion of a contact strip 172 not wrapped around the lead body 106, can be removed by any process known to those of skill in the art such as, for example, using a press, using a die, or the like.

In some embodiments, a portion of the contact strip 172 is inserted into a slit 186 and is coupled to a conductor 128 and another portion of the contact strip 172 is wrapped around the lead body 106 to form one or more layers of the contact strip 172 around the lead body 106 as illustrated schematically in FIG. 14.

In some embodiments, a method of making a lead includes sealing at least one seam 138 of the contact strip 172 wrapped around the lead body. In some embodiments, a seam 138 of a contact strip 172 is illustrated schematically in FIGS. 6 and 14. The seam 138 can be sealed using any method known to those of skill in the art such as, for example, welding (e.g., spot welding), soldering, crimping, using adhesives, and the like.

If one or more contact strips 172 are wrapped around a lead body 106 that is isodiametric, the resulting lead can optionally have a larger diameter D2 (see FIG. 10) at the portion of the lead where the contact strip 172 is wrapped around the lead body 106 than the diameter D1 (see FIG. 10) at a portion of the lead where no contact strip 172 is wrapped around the lead body 106. As described above, in some embodiments, a portion of the lead body 106 is removed before at least one contact strip 172 is wrapped around the lead body 106. The thickness T1 of the portion of the lead body 106 that is removed can optionally be such that the lead will be isodiametric after one or more contact strips 172 are wrapped around the lead body 106 as illustrated schematically in FIGS. 4 and 5.

Turning to FIG. 11, in some embodiments, a method of making a lead comprises disposing a biocompatible material 164 over at least a portion of the lead body 106. The biocompatible material 164 can optionally be disposed over at least one portion of a lead body 106 that is not wrapped by a contact strip 172. For example, the biocompatible material 164 can optionally be disposed over each portion of the lead body 106 that is not wrapped by a contact strip 172 as illustrated schematically in FIG. 11.

The biocompatible material 164 disposed over at least a portion of the lead body 106 may have any thickness. The biocompatible material 164 can optionally be disposed over the lead body 106 such that the resulting lead is isodiametric as illustrated schematically in FIG. 11. For example, the biocompatible material 164 can optionally be disposed over at least one portion of the lead body 106 that is not wrapped by a contact strip 172 and can optionally be disposed over the lead body 106 such that a thickness T2 (see FIG. 11) of the biocompatible material 164 is equal to one half of the increase in diameter of the lead resulting from the wrapped contact strip 172, such that the resulting lead is isodiametric.

Figure 15:
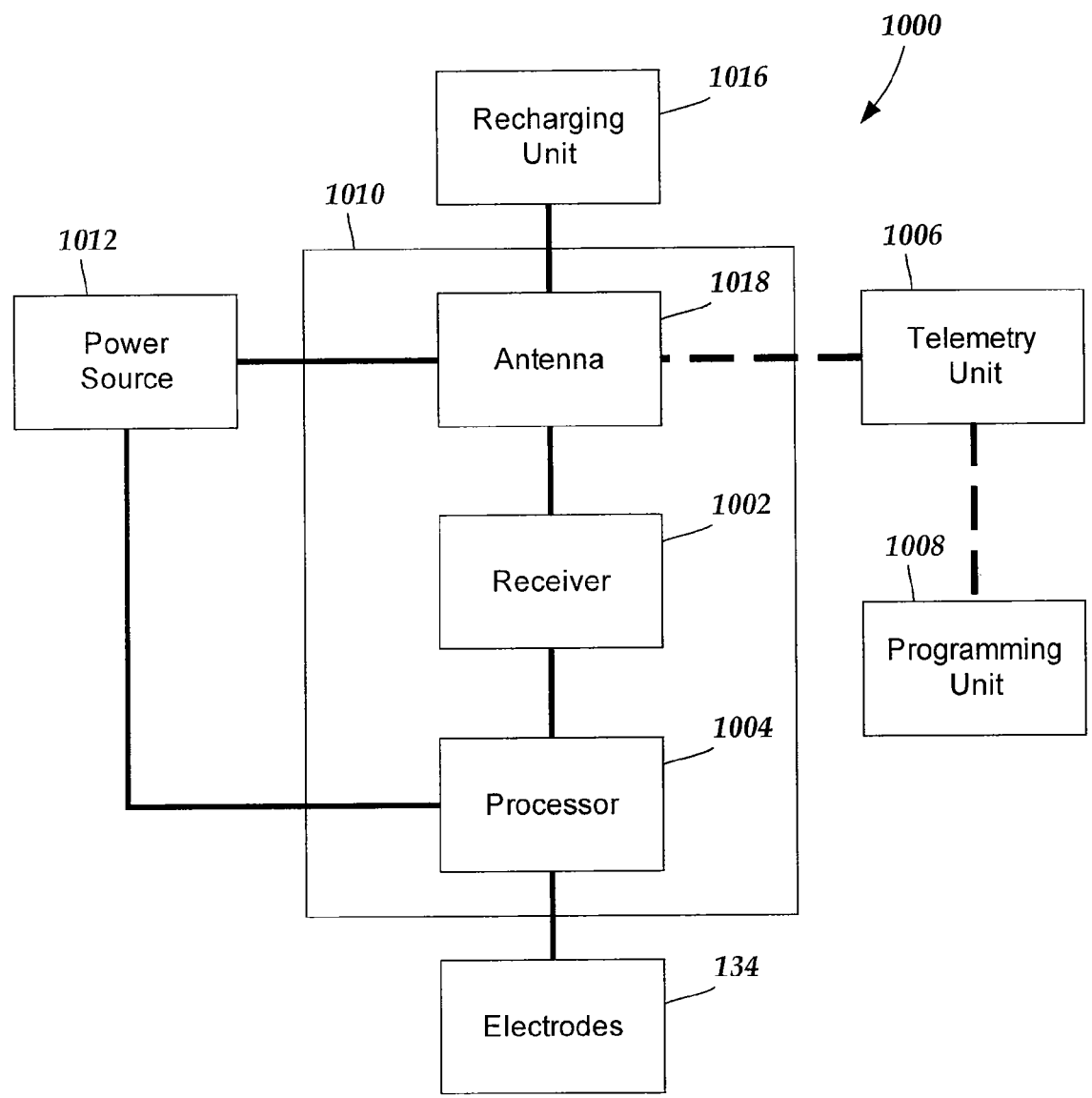
FIG. 15 is a schematic overview of one embodiment of components of a stimulation system, including an electronic subassembly disposed within a control module, according to the invention.

FIG. 15 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making a lead comprising:
    forming a slit in a lead body, wherein the lead body defines at least one lumen extending along the length of the lead body, wherein a plurality of conductors are disposed in the at least one lumen, and wherein the slit extends from an exterior of the lead body to a one of the at least one lumen;
    inserting a portion of a contact strip into the slit;
    contacting the portion of the contact strip with at least one of the plurality of conductors; and
    wrapping the contact strip around the lead body two or more times to form two or more layers of the contact strip around the lead body, wherein each of the times that the contact strip is wrapped around the lead body forms a new one of the two or more layers which is disposed over each preceding layer of the two or more layers.

2. The method of claim 1,
    wherein forming a slit comprises forming a plurality of slits in the lead body, each slit extending from the exterior of the lead body to one of the at least one lumen,
    wherein inserting a portion of a contact strip into the slit comprises inserting a portion of each of two or more contact strips into a different one of the plurality of slits in the lead body, and
    wherein wrapping the contact strip around the lead body comprises wrapping each of the two or more contact strips around the lead body simultaneously.

3. The method of claim 1, further comprising sealing a seam of the wrapped contact strip.

4. The method of claim 1, further comprising disposing a biocompatible material over each portion of the lead body that is not wrapped by the contact strip after wrapping the contact strip around the lead body, such that the resulting lead is isodiametric.

5. The method of claim 1, wherein the contact strip wrapped around the lead body forms an electrode and the contract strip and the electrode have a same width.

6. The method of claim 1, wherein the contact strip wrapped around the lead body forms a terminal and the contact strip and the terminal have a same width.

7. A method of making a lead comprising:
    disposing one or more conductors in a first lumen of a lead body;

forming a first slit from an exterior of the lead body to the first lumen to access a portion of at least one of the one or more conductors disposed in the first lumen;

attaching a first contact strip to the portion of at least one of the one or more conductors, wherein the contact strip is unconnected to the one or more conductors prior to attaching; and wrapping the first contact strip around the lead body two or more times to form two or more layers of the first contact strip around the lead body, wherein each of the times that the contact strip is wrapped around the lead body forms a new one of the two or more layers which is disposed over each preceding layer of the two or more layers.

8. The method of claim 7, further comprising:

disposing one or more conductors in a second lumen of the lead body;

forming a second slit from an exterior of the lead body to the second lumen to access a portion of at least one of the one or more conductors disposed in the second lumen;

coupling a second contact strip to the portion of at least one of the one or more conductors disposed in the second lumen; and wrapping the second contact strip around the lead body, wherein the second contact strip is flat prior to wrapping.

9. The method of claim 8, wherein the first contact strip and the second contact strip are wrapped around the lead body simultaneously.

10. The method of claim 7, wherein the first contact strip is planar prior to wrapping.

11. The method of claim 7, wherein attaching a first contact strip to the portion of at least one of the one or more conductors comprises attaching a contact strip, having a rectangular major surface, to the portion of at least one of the one or more conductors.

12. The method of claim 7, further comprising sealing a seam of the wrapped first contact strip.

13. The method of claim 7, further comprising:

forming a second slit from the exterior of the lead body to the first lumen, wherein the second slit is formed at a distal end of the lead body;

coupling a second contact strip to a portion of at least one of the one or more conductors disposed in the first lumen of the lead body; and wrapping the second contact strip around a distal end of the lead body, wherein forming a first slit comprises forming a first slit at a proximal end of the lead body, wherein coupling a first contact strip to the portion of at least one of the one or more conductors comprises coupling the first contact strip to the portion of at least one of the one or more conductors at a proximal end of the lead body, and wherein wrapping the first contact strip around the lead body comprises wrapping the first contact strip around a proximal end of the lead body.

14. The method of claim 7, wherein the contact strip wrapped around the lead body forms an electrode and the contact strip and the electrode have a same width.

15. The method of claim 7, wherein the contact strip wrapped around the lead body forms a terminal and the contact strip and the terminal have a same width.

* * * * *